(12) United States Patent
Muser et al.

(10) Patent No.: US 11,510,686 B2
(45) Date of Patent: Nov. 29, 2022

(54) RETROGRADE DRILLING DEVICE

(71) Applicant: CONMED CORPORATION, Utica, NY (US)

(72) Inventors: Andrew Muser, St. Pete Beach, FL (US); Andrew Kam, Odessa, FL (US)

(73) Assignee: CONMED CORPORATION, Utica, NY (US)

( * ) Notice: Subject to any disclaimer, the term of this patent is extended or adjusted under 35 U.S.C. 154(b) by 273 days.

(21) Appl. No.: 16/502,060

(22) Filed: Jul. 3, 2019

(65) Prior Publication Data
US 2020/0008814 A1  Jan. 9, 2020

Related U.S. Application Data

(60) Provisional application No. 62/842,700, filed on May 3, 2019, provisional application No. 62/694,059, filed on Jul. 5, 2018.

(51) Int. Cl.
*A61B 17/16* (2006.01)
*A61B 17/00* (2006.01)

(52) U.S. Cl.
CPC ...... *A61B 17/1631* (2013.01); *A61B 17/1615* (2013.01); *A61B 2017/00477* (2013.01)

(58) Field of Classification Search
CPC .......................................... A61B 17/16–171697
See application file for complete search history.

(56) References Cited

U.S. PATENT DOCUMENTS

| | | | |
|---|---|---|---|
| 8,070,750 B2 | 12/2011 | Wenstrom, Jr. et al. | |
| 8,118,814 B2 | 2/2012 | Oren et al. | |
| 8,529,567 B2 | 9/2013 | Garcia et al. | |
| 8,540,724 B2 | 9/2013 | Mast et al. | |
| 8,591,514 B2 * | 11/2013 | Sherman ............ | A61B 17/1617 606/80 |
| 8,790,361 B2 | 7/2014 | Spenciner et al. | |
| 8,926,643 B2 | 1/2015 | Spenciner et al. | |
| 9,011,443 B2 | 4/2015 | Whittaker et al. | |
| 9,072,528 B2 | 7/2015 | Cournoyer et al. | |
| 9,084,615 B2 | 7/2015 | Cleveland et al. | |
| 9,101,366 B2 * | 8/2015 | Sterrett ................. | A61B 17/16 |
| 9,226,759 B2 | 1/2016 | Whittaker et al. | |
| 9,364,260 B2 | 6/2016 | Cleveland et al. | |
| 9,414,850 B2 | 8/2016 | Cleveland et al. | |
| 9,668,750 B2 * | 6/2017 | Mirochinik ........ | A61B 17/1796 |
| 9,795,395 B2 * | 10/2017 | Lizardi .............. | A61B 17/1675 |

(Continued)

*Primary Examiner* — Zade Coley
(74) *Attorney, Agent, or Firm* — Bond, Schoeneck & King, PLLC; Frederick J. M. Price

(57) ABSTRACT

A drill assembly for creating a reverse counterbore bone tunnel while increasing bone preservation. The drill assembly including a housing having an actuation mechanism and a cannulated shaft connected to the actuation mechanism. The drill assembly also includes a rigid rod extending through the cannulated shaft. Engaging the actuation mechanism moves the cannulated shaft along the rigid rod. The drill assembly additionally includes a distal tip connected to the cannulated shaft and the rigid rod. Proximal movement of the cannulated shaft along the rigid rod causes the distal tip to rotate from a first configuration to a second configuration. In the second configuration, the distal tip extends at an angle relative to the cannulated shaft.

19 Claims, 23 Drawing Sheets

(56) References Cited

U.S. PATENT DOCUMENTS

| | | |
|---|---|---|
| 10,022,174 B2 | 7/2018 | Fifolt |
| 10,105,150 B2 * | 10/2018 | Bourque ............ A61B 17/1714 |
| 10,188,403 B2 | 1/2019 | Mirochinik et al. |
| 10,292,724 B2 | 5/2019 | Cournoyer et al. |
| 10,335,168 B2 | 7/2019 | Lizardi et al. |
| 10,537,340 B2 | 1/2020 | Mirochinik et al. |
| 10,695,073 B2 * | 6/2020 | Adams ................ A61B 17/1617 |
| 2005/0240193 A1 * | 10/2005 | Layne ................. A61B 17/1671 606/80 |
| 2006/0074434 A1 | 4/2006 | Wenstrom et al. |
| 2009/0171359 A1 * | 7/2009 | Sterrett ............. A61B 17/1675 606/80 |
| 2014/0228849 A1 * | 8/2014 | Sterrett .................. A61B 17/16 606/80 |
| 2014/0276844 A1 * | 9/2014 | Bourque ............ A61B 17/1615 606/80 |
| 2015/0351777 A1 * | 12/2015 | Lizardi .............. A61B 17/1622 606/80 |
| 2016/0256192 A1 | 9/2016 | Cleveland et al. |
| 2017/0150976 A1 * | 6/2017 | Sterrett .................. A61B 90/06 |
| 2018/0008287 A1 * | 1/2018 | Lizardi .............. A61B 17/1675 |
| 2018/0221032 A1 | 8/2018 | Garcia et al. |
| 2019/0038299 A1 * | 2/2019 | Bourque ............ A61B 17/1615 |
| 2019/0059910 A1 * | 2/2019 | Adams ................ A61B 17/1624 |
| 2019/0167281 A1 | 6/2019 | Zilberman et al. |

\* cited by examiner

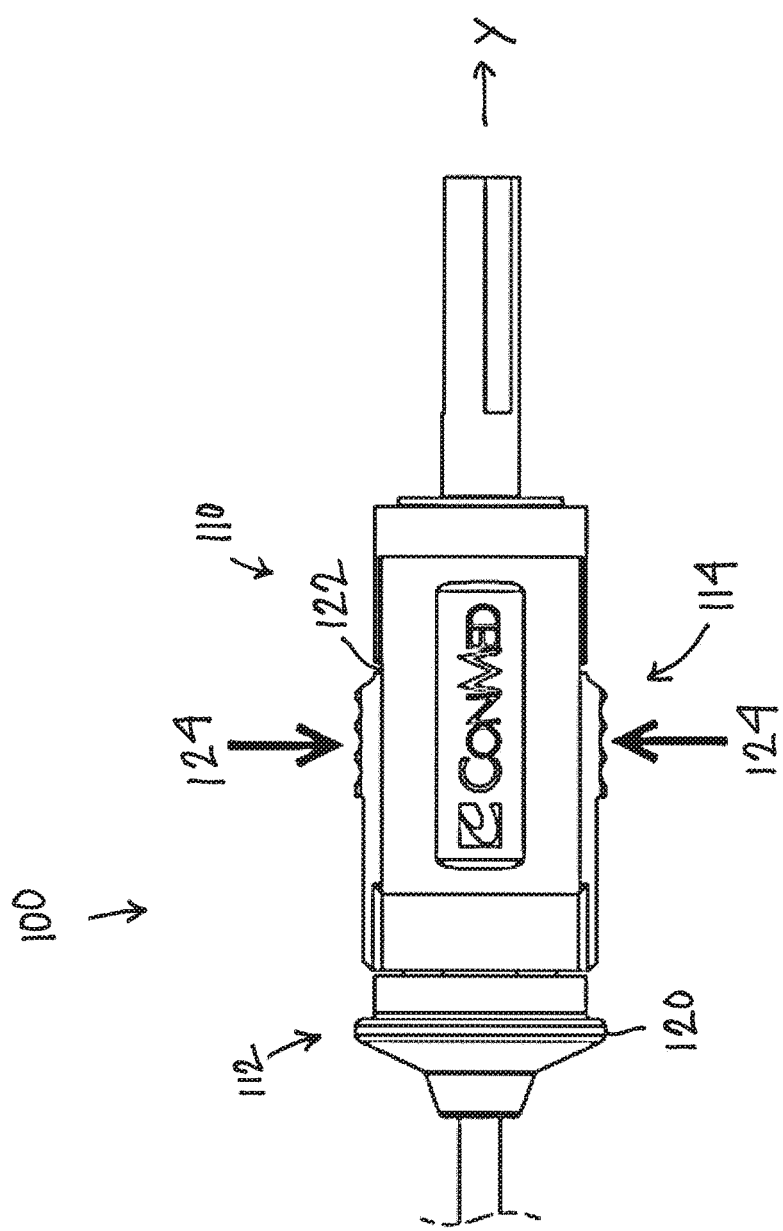
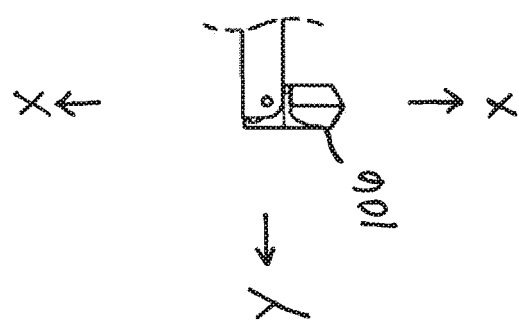
FIG. 4

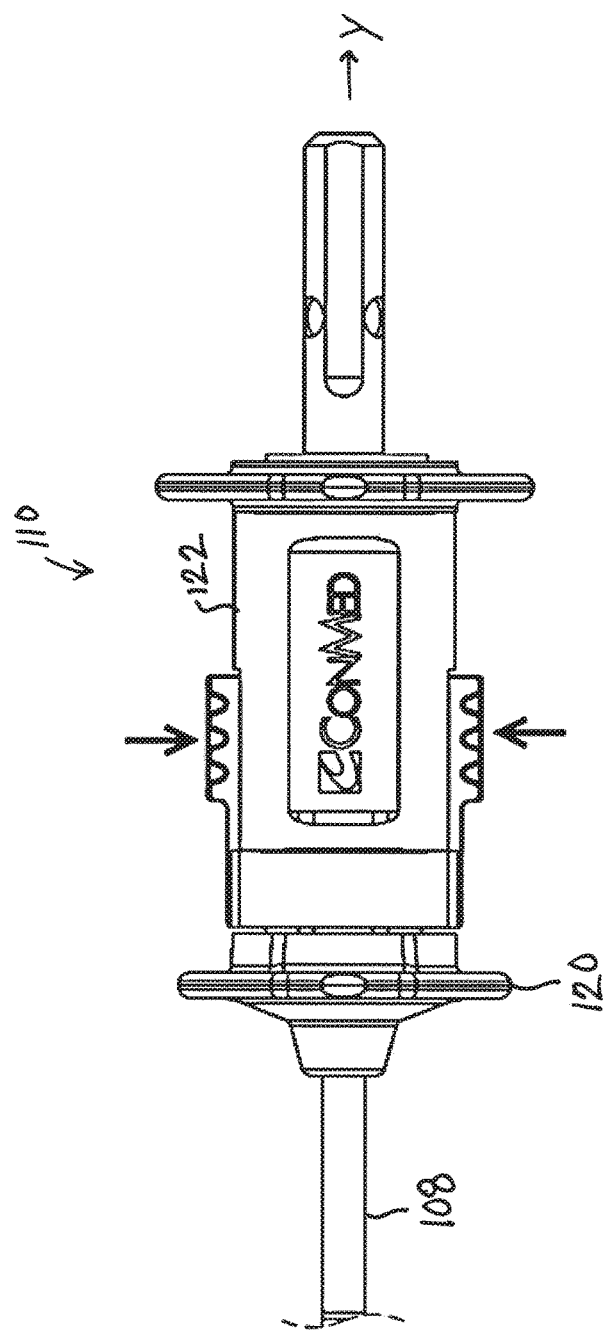
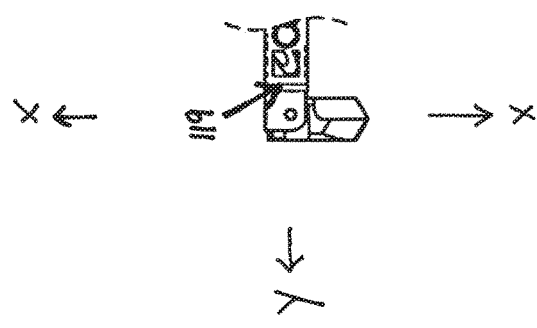
FIG. 13

RETROGRADE DRILLING DEVICE

CROSS-REFERENCE TO RELATED APPLICATIONS

This application claims priority to U.S. Provisional Patent Application Ser. No. 62/694,059, filed on Jul. 5, 2018 and entitled "Retrograde Drilling Device" and U.S. Provisional Patent Application Ser. No. 62/842,700, filed on May 3, 2019 and entitled "Retrograde Drilling Device," the entireties of which are incorporated herein by reference.

BACKGROUND OF THE INVENTION

1. Field of the Invention

The present invention is directed generally to a surgical system and, more particularly, to a drill assembly for creating a reverse counterbore bone tunnel while increasing bone preservation.

2. Description of Related Art

Drilling devices are used to generate retrograde bone tunnels for orthopedic surgical procedures. Specifically, there are orthopedic procedures requiring reshaping or resecting bones in order to create sockets and tunnels in preparation for ligament reconstruction. For example, a bone tunnel is required for a knee ligament reconstruction procedure. Conventional methods for creating the bone tunnel include using a rotary cutting instrument to drill the tunnel. Drilling the bone tunnel results in removal of a significant amount of bone material from the patient. The loss of bone material is additional trauma to the patient. Additional trauma increases the length of the surgical procedure, the pain felt by the patient, and the time required for recovery.

Therefore, there is a need for a device for creating a reverse counterbore bone tunnel while increasing bone preservation.

Description of the Related Art Section Disclaimer: To the extent that specific patents/publications/products are discussed above in this Description of the Related Art Section or elsewhere in this disclosure, these discussions should not be taken as an admission that the discussed patents/publications/products are prior art for patent law purposes. For example, some or all of the discussed patents/publications/products may not be sufficiently early in time, may not reflect subject matter developed early enough in time and/or may not be sufficiently enabling so as to amount to prior art for patent law purposes. To the extent that specific patents/publications/products are discussed above in this Description of the Related Art Section and/or throughout the application, the descriptions/disclosures of which are all hereby incorporated by reference into this document in their respective entirety(ies).

SUMMARY OF THE INVENTION

Embodiments of the present invention are directed to a drill assembly for creating a reverse counterbore bone tunnel while increasing bone preservation. According to one aspect, the present invention is a drill assembly including a housing having an actuation mechanism and a cannulated shaft connected to the actuation mechanism. The drill assembly also includes a rigid rod extending through the cannulated shaft. Engaging the actuation mechanism moves the cannulated shaft along the rigid rod. The drill assembly additionally includes a distal tip connected to the cannulated shaft and the rigid rod. Proximal movement of the cannulated shaft along the rigid rod causes the distal tip to rotate.

According to another aspect, the drill assembly includes a housing having a cap, a body, and a cannulated shaft connected to the cap. The drill assembly also includes a rigid rod extending through the cannulated shaft and the cap. The rigid rod is connected to the body of the housing such that the cannulated shaft is slidable along the rigid rod. Proximal movement of the cap causes proximal movement of the cannulated shaft along the rigid rod. The drill assembly additionally includes a distal tip connected to the cannulated shaft and the rigid rod. Proximal movement of the cap and the cannulated shaft along the rigid rod causes the distal tip to rotate from a first configuration to a second configuration.

According to yet another aspect, the drill assembly includes a housing having a cap, a body, and an elongated core movable within the body. The elongated core has a cannulated shaft connected thereto and extending therefrom. The cannulated shaft connects to and extends through the cap. The drill assembly also includes a rigid rod extending through the cannulated shaft and the cap. The rigid rod is connected to a proximal end of the body. The cannulated shaft and the cap are slidable along the rigid rod. The drill assembly additionally includes a distal tip connected to the cannulated shaft and the rigid rod. Proximal movement of the cap and the cannulated shaft along the rigid rod causes the distal tip to rotate from a first configuration to a second configuration. In the second configuration, the distal tip extends at an angle relative to the cannulated shaft.

These and other aspects of the invention will be apparent from and elucidated with reference to the embodiment(s) described hereinafter.

BRIEF DESCRIPTION OF THE DRAWINGS

One or more aspects of the present invention are particularly pointed out and distinctly claimed as examples in the claims at the conclusion of the specification. The foregoing and other objects, features, and advantages of the invention are apparent from the following description taken in conjunction with the accompanying drawings in which:

FIG. 4 is a side view schematic representation of the drill assembly in a second configuration, according to an embodiment;

FIG. 13 is a side view schematic representation of the drill assembly in a second configuration, according to an alternative embodiment;

DETAILED DESCRIPTION OF THE INVENTION

Aspects of the present invention and certain features, advantages, and details thereof, are explained more fully below with reference to the non-limiting examples illustrated in the accompanying drawings. Descriptions of well-known structures are omitted so as not to unnecessarily obscure the invention in detail. It should be understood, however, that the detailed description and the specific non-limiting examples, while indicating aspects of the invention, are given by way of illustration only, and are not by way of limitation. Various substitutions, modifications, additions, and/or arrangements, within the spirit and/or scope of the underlying inventive concepts will be apparent to those skilled in the art from this disclosure.

Figure 1:
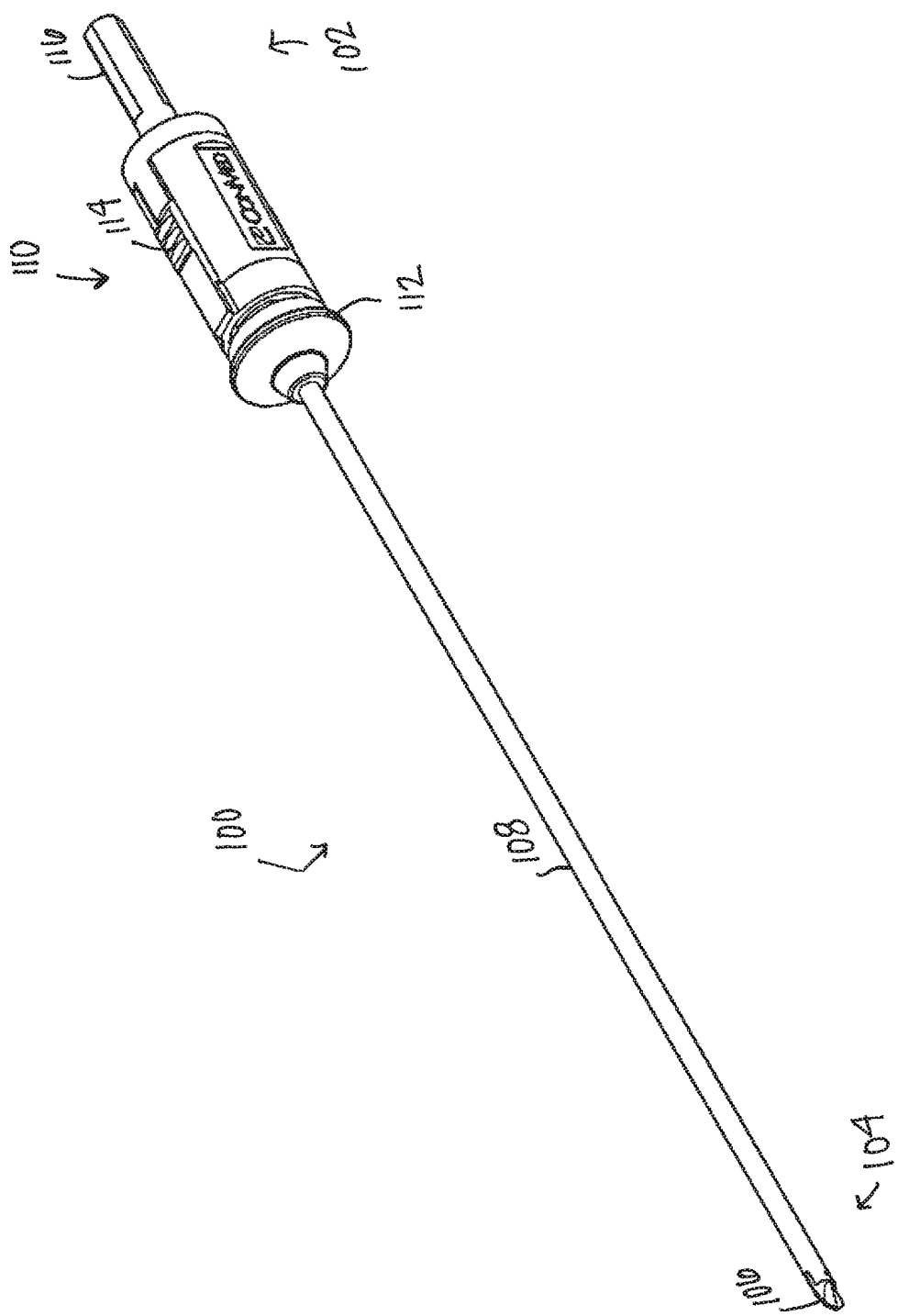
FIG. 1 is a perspective view schematic representation of a drill assembly, according to an embodiment.

Referring now to the figures, wherein like reference numerals refer to like parts throughout, FIG. 1 shows a perspective view schematic representation of a drill assembly 100, according to an embodiment. The drill assembly 100 in FIG. 1 is a retro-drill assembly for generating retrograde bone tunnels. Clockwise rotation of the drill assembly 100 performs forward drilling and counterbore reaming. The drill assembly 100 comprises a proximal end 102 for connection to a surgical drill and a distal end 104 for engaging a bone. The distal end 104 comprises a drill tip 106 for drilling into the bone. The drill tip 106 is connected to an elongated cannulated shaft 108, which extends in the proximal direction.

Still referring to FIG. 1, the cannulated shaft 108 extends and connects to a housing 110. In the depicted embodiment, the housing 110 is cylindrical to provide an improved ergonomic grip for the surgeon; however, the housing 110 may be any suitable geometric configuration. The housing 110 includes an actuation mechanism 112 and a release mechanism 114 for moving the drill tip 106 between different configurations, as described in detail below. As also shown in FIG. 1, the proximal end 102 of the drill assembly 100 comprises a shank 116, which extends proximally from the housing 110. The drill assembly 100 is attached to a surgical drill (not shown) by tightening the jaws of the surgical drill around the shank 116. For example, a Jacobs chuck attachment can be used. Additionally, the shank 116 may comprise features that allow it to be attached to the surgical drill using a "quick-connect" attachment, such as a Trinkle, AO, Hudson, Zimmer, or Harris. The embodiment shown in FIG. 1 uses a Trinkle adapter.

Figure 2:
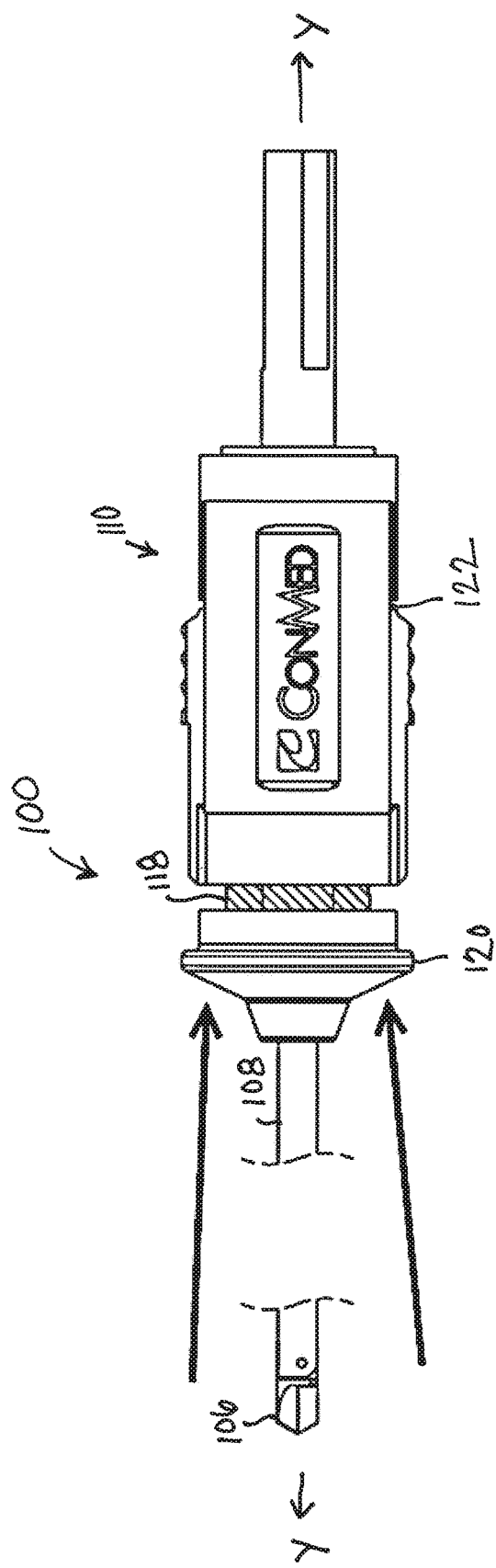
FIG. 2 is a side view schematic representation of the drill assembly in a first configuration, according to an embodiment.
Figure 3:
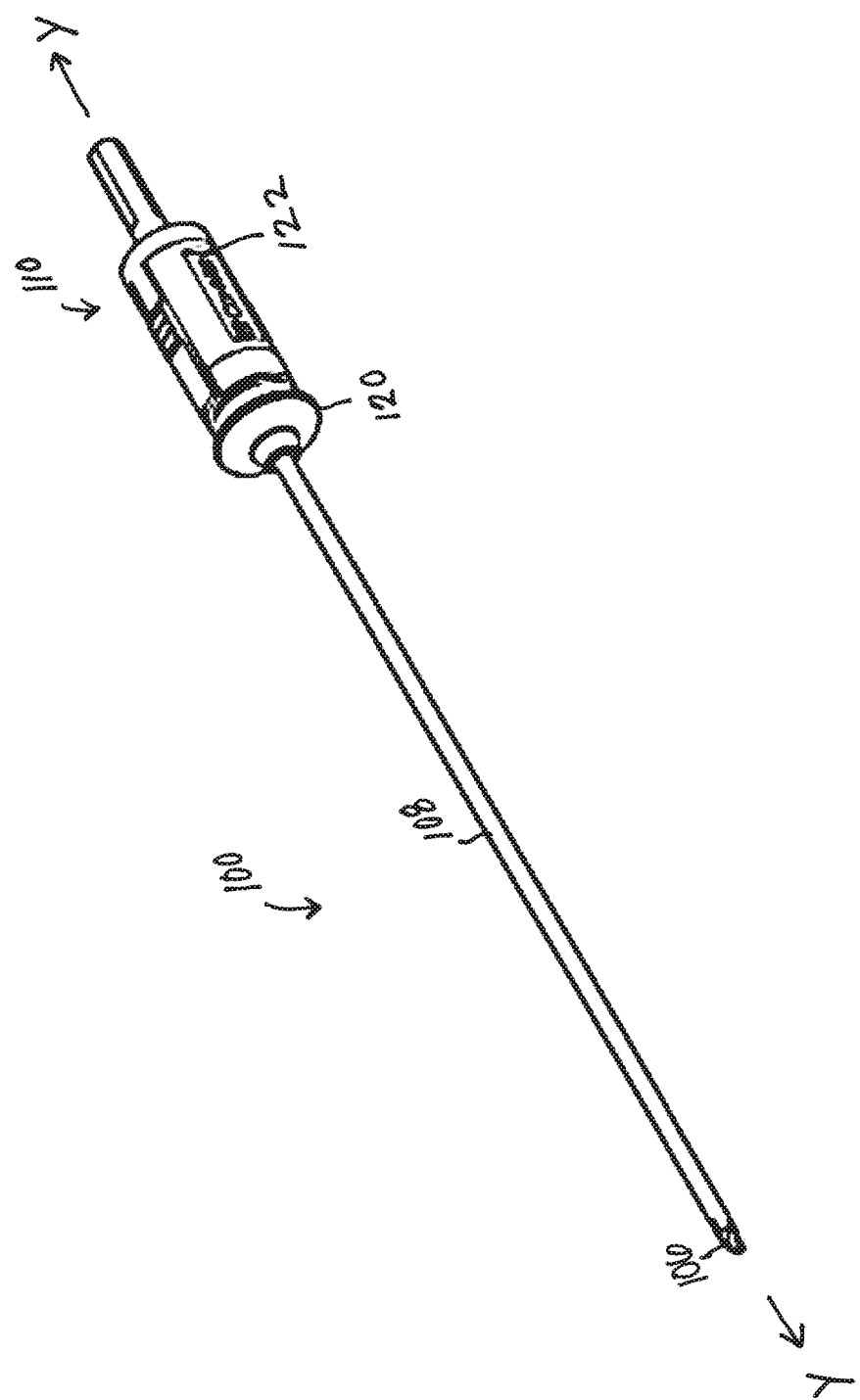
FIG. 3 is a perspective view schematic representation of the drill assembly in a first configuration, according to an embodiment.

Turning now to FIGS. 2 and 3, there are shown side and perspective views schematic representations of the drill assembly 100 in a first configuration, according to an embodiment. In the first configuration, the entire drill assembly 100 extends substantially along a central longitudinal y-y axis, as shown in FIGS. 2 and 3. In an embodiment, the first configuration is a 0 degree position such that the drill tip 106 does not extend at an angle relative to the cannulated shaft 108 (or drill assembly 100). In the first configuration, an indicator 118 is visible at the housing 110. Specifically, as shown in FIG. 2, the indicator 118 is a portion or region of the housing 110 extending between a distal cap 120 of the housing 110 and a proximal body 122 of the housing 110.

Still referring to FIG. 2, the cap 120 is movable along the central longitudinal y-y axis. When the cap 120 is in the first configuration (i.e., its most distal position), the indicator 118 is exposed. The indicator 118 serves as notice to the surgeon that the drill tip 106 is in the first configuration (i.e., 0 angle position) as the orientation of the drill tip 106 may not be clearly visible at the surgical site. In the first configuration, the drill assembly 100 can be used to drill a conventional hole or bone tunnel.

Figure 5:
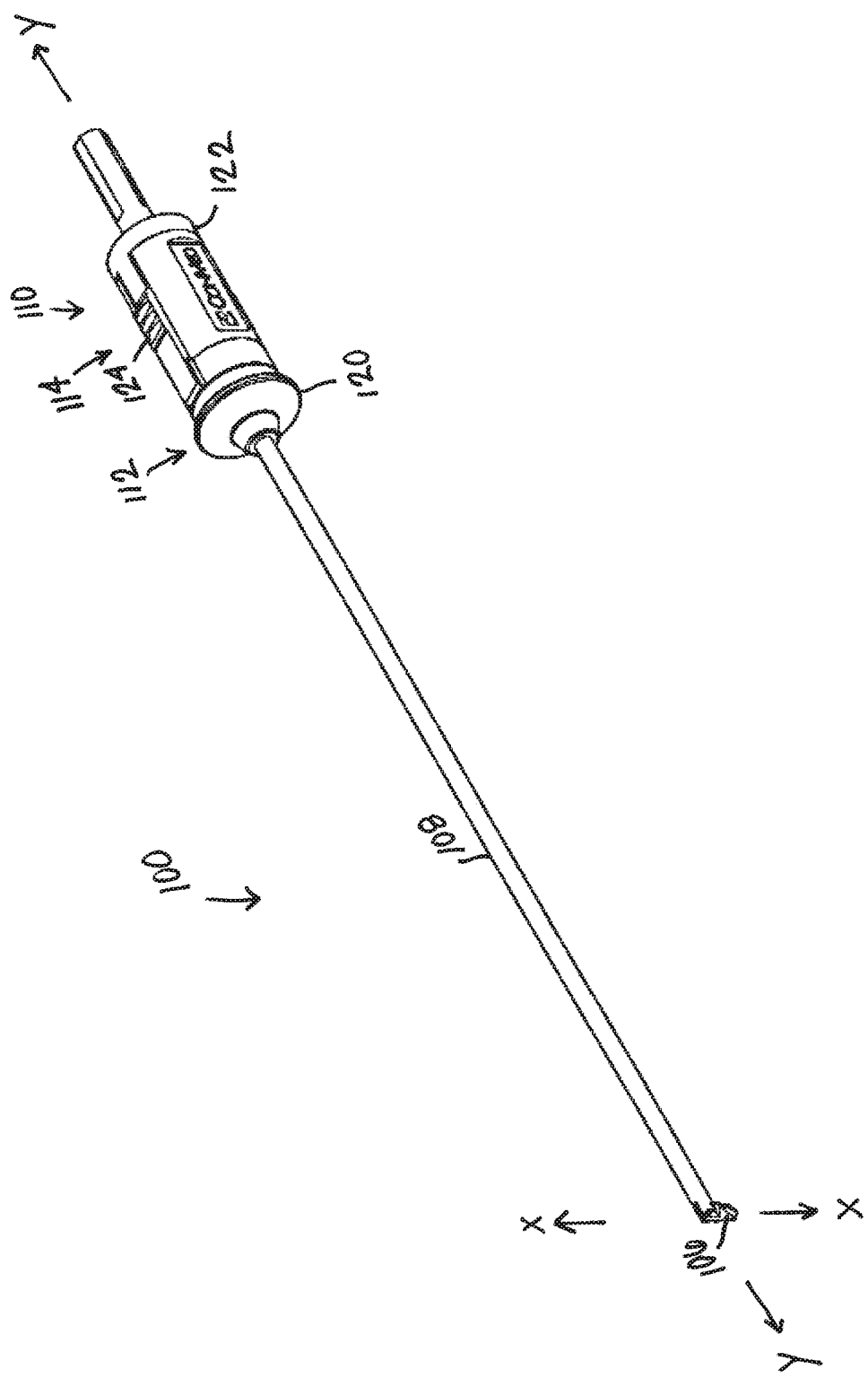
FIG. 5 is a perspective view schematic representation of the drill assembly in a second configuration, according to an embodiment.

Turning now to FIGS. 4 and 5, there are shown side and perspective views schematic representations of the drill assembly 100 in a second configuration, according to an embodiment. From the first configuration (FIGS. 2-3), the drill tip 106 is actuated to move the drill assembly 100 to the second configuration. To move the drill assembly 100 to the second configuration, the cap 120, serving as the actuation mechanism 112, is pulled in the proximal direction until a locking mechanism (not shown) is engaged. In an embodiment, the locking mechanism is an internal catch (described below) within the housing 110 that, when engaged, retains the cap 120 at or connected to the body 122 of the housing 110, as shown in FIG. 4. Thus, in the second configuration, the indicator 118 is not visible. In the embodiment shown in FIGS. 4 and 5, the indicator 118 is covered or hidden within the housing 110. In an embodiment, engaging the internal catch causing an audible snapping sound that also serves as an indication of the configuration of the drill assembly 100.

In the second configuration, as shown in FIG. 5, the drill tip 106 extends at an angle relative to the cannulated shaft 108 (or drill assembly 100) and the central longitudinal y-y axis. In an embodiment, the second configuration, as shown in FIGS. 4 and 5, is a 90 degree position such that the drill tip 106 extends along a lateral x-x axis, which is 90 degrees or substantially perpendicular relative to the cannulated shaft 108 (or drill assembly 100) and the central longitudinal y-y axis. In the second configuration, the drill assembly 100 can be used for counterbore drilling. A counterbored bone tunnel removes less bone material from the patient. The benefits of a counterbore bone tunnel over a straight bore hole include less pain, faster recovery, and increased bone preservation.

To move the drill assembly 100 from the second configuration back to the first configuration, the locking mechanism of the housing 110 is released by engaging the release mechanism 114. To release the locking mechanism of the housing 110, release tabs 124 (of the release mechanism 114) on the housing 110 are engaged. As shown in FIG. 4, the body 122 of the housing 110 comprises a pair of release tabs 124 on opposing sides. When the release tabs 124 are pressed toward the body 122 of the housing 110, the cap 120 is released and moves in the distal direction away from the body 122 to the first configuration.

Figure 6A:
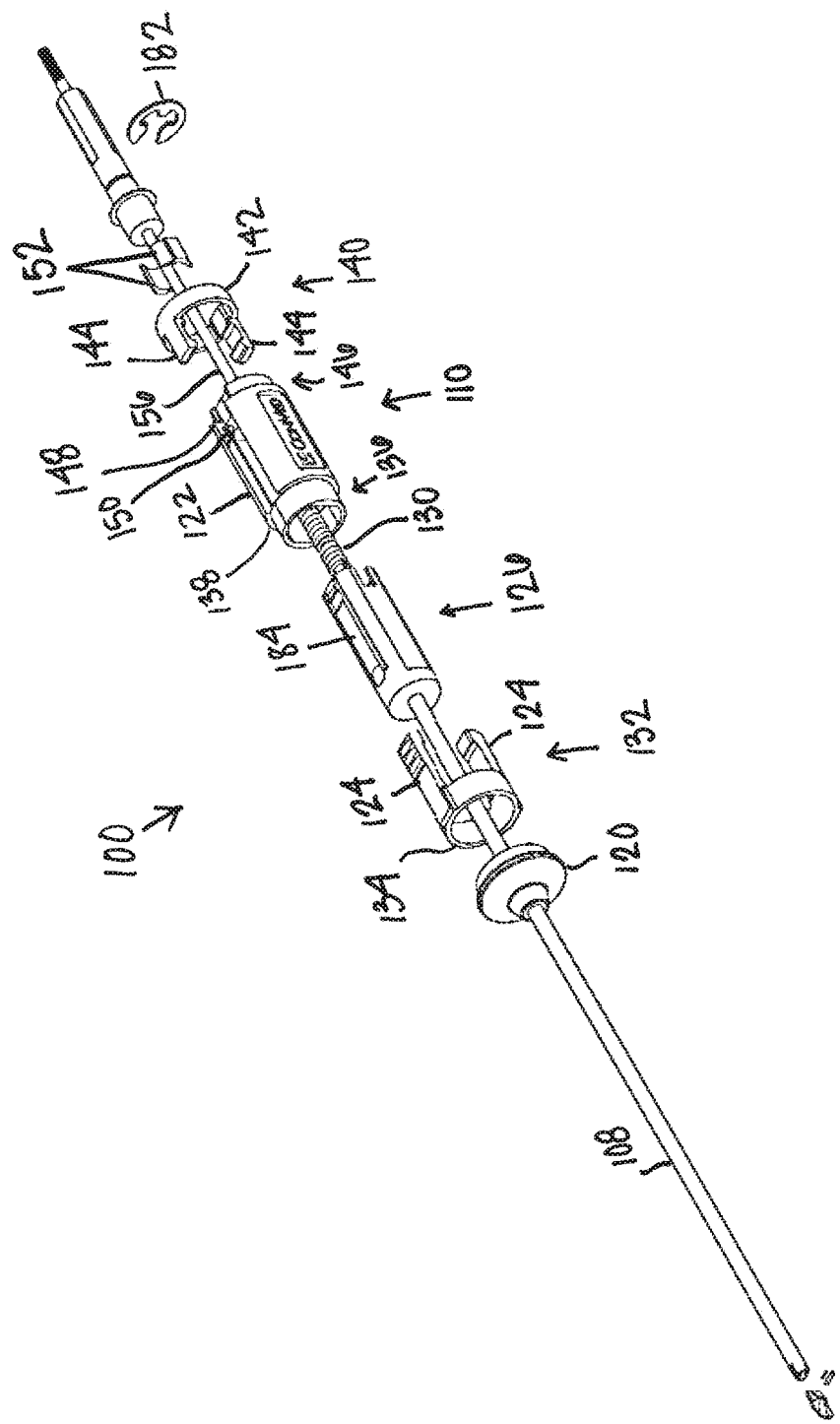
FIG. 6A is an exploded view schematic representation of the drill assembly in the first configuration, according to an embodiment.

Referring now to FIG. 6A, there is shown an exploded view schematic representation of the drill assembly 100 in the first configuration, according to an embodiment. FIG. 6A provides a detailed view of the internal catch and components of the housing 110. In the depicted embodiment, the housing 110 comprises a core 126. The core 126 is a cylindrical piece with a pair of tangs 184 (only one is shown) extending along at least a portion of its length. (The tangs 184 and their function as the locking mechanism are discussed in detail below with regard to the embodiment of the drill assembly 100 shown in FIGS. 10-22). The core 126 is securely attached to the cannulated shaft 108 and a rigid rod 156 extends through the core 126 and the cannulated shaft 108. The core 126 is sized and configured to move within the body 122 of the housing 110. The core 126 is also rigidly attached to the cap 120 so that when the cap 120 moves along the central longitudinal y-y axis, the core 126 moves as well. A spring 130 is positioned proximally relative to the core 126 in the body 122 of the housing 110. In the first configuration, the spring 130 is extended and in the second configuration, the spring 130 is compressed.

Still referring to FIG. 6A, the housing 110 also comprises a release 132 between the body 122 of the housing 110 and the cap 120. The release 132 is a ring 134 with the opposing release tabs 124 extending proximally therefrom. The ring 134 is sized and configured to fit around the core 126 and the release tabs 124 are sized and configured to slide over the core 126. The ring 134 of the release 132 is also sized and configured to fit around a distal end 136 of the body 122 of the housing 110 up to and abutting a distal edge 138 of the body 122. The release 132 holds the housing 110 together (if it is more than one piece) and releases the locking mechanism (as discussed in detail below) by transmitting force to the core 126.

Figure 6B:
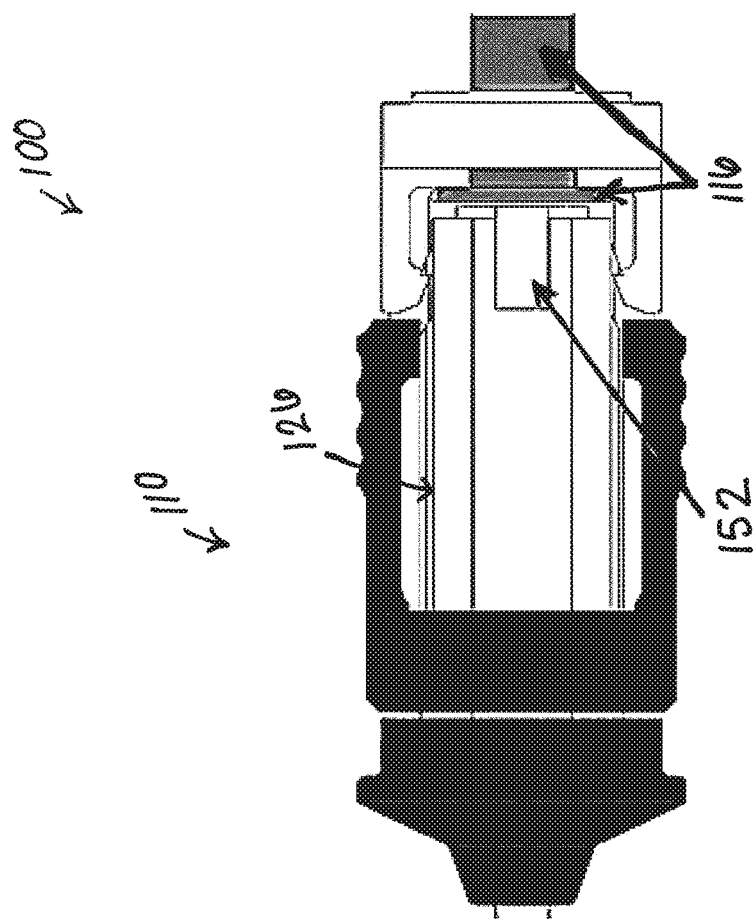
FIG. 6B is a partial cross-sectional side view schematic representation of the housing of the drill assembly in the second configuration, according to an embodiment.

The drill assembly 100 in FIG. 6A also comprises a proximal catch 140. The proximal catch 140 is a ring 142 with one or more catching tabs 144 extending distally therefrom. In the depicted embodiment, the proximal catch 140 has two catching tabs 144. The catching tabs 144 are configured to lock into the body 122 of the housing 110. Specifically, the ring 142 of the proximal catch 140 is sized and configured to fit around a proximal end 146 of the body 122 of the housing 110 up to and abutting a proximal edge 148 of the body 122, while the catching tabs 144 snap into a recess 150 in the body 122. In an embodiment, the housing 110 also includes one or more shims 152 or any other tapered or wedged piece of material for filling in gaps between components of the housing 110. In the depicted embodiment, a pair of shims 152 are between a proximal end 154 of the body 122 and the proximal catch 140. In another embodiment, shown in FIG. 6B, the shims 152 are located between the core 126 and the shank 116. Specifically, the shims 152 in FIG. 6B fill the space between the core 126 and the shank 116. The shims 152 increase the stability of the drill assembly 100; however, they are not required. Similarly, a retaining ring 182 may be used to secure the proximal catch 140 to the rigid rod 156.

Figure 7:
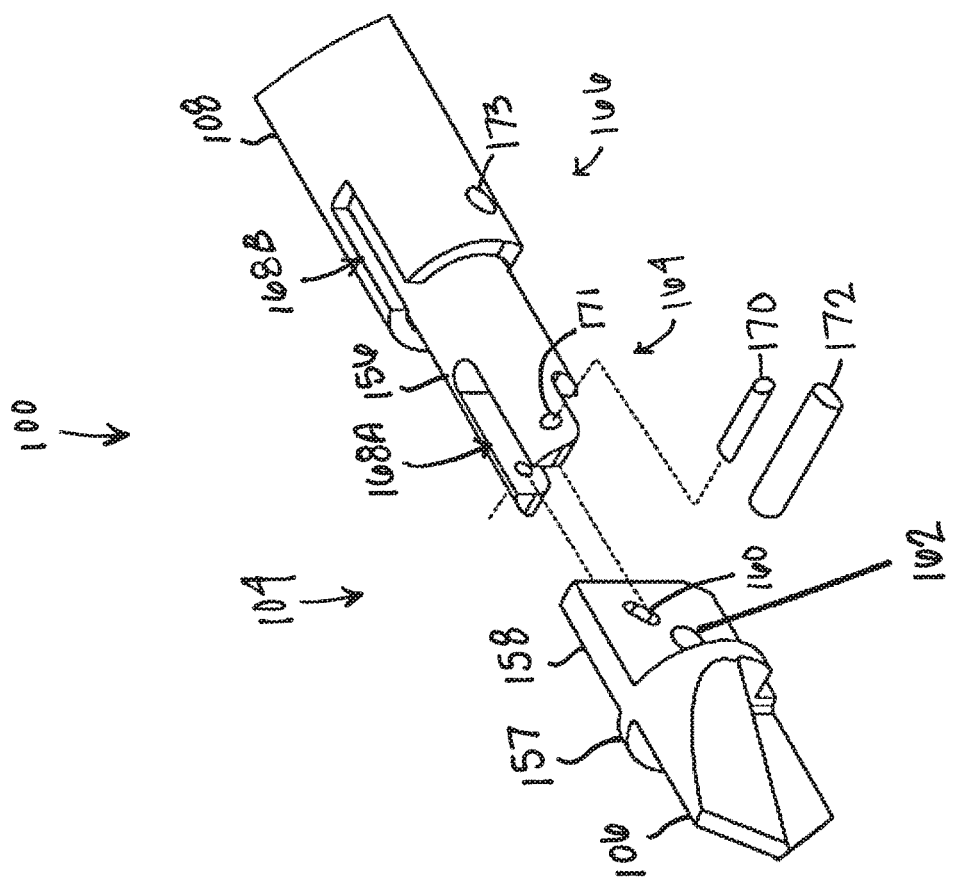
FIG. 7 is an exploded perspective view schematic representation of the distal end of the drill assembly, according to an embodiment.

Turning now to FIG. 7, there is shown an exploded perspective view schematic representation of the distal end 104 of the drill assembly 100, according to an embodiment. The distal end 104 comprises the drill tip 106 connected to the cannulated shaft 108 and the rigid rod 156. The rigid rod 156 is positioned within the cannulated shaft 108 to keep the particulate and other biological material out of the cannulated shaft 108. The drill tip 106 has a flat outer diameter 157 and a flat connecting portion 158 with a first aperture 160 spaced from a second aperture 162. In the depicted embodiment, the flat outer diameter 157 is larger than an outer diameter of the cannulated shaft 108, which reduces friction on the cannulated shaft 108. In another embodiment, the flat outer diameter 157 matches an outer diameter of the cannulated shaft 108. In yet another embodiment, the outer diameter of the cannulated shaft 108 comprises sections with a reduced outer diameter to allow for bone chips to clear the area of the cannulated shaft 108 (similar to a drill bit). However, it may be difficult to achieve sections of a reduced outer diameter in the cannulated shaft 108 as a thin-walled cannulated shaft 108 has various geometric constraints. As additionally shown in FIG. 7, a distal end 164 of the rigid rod 156 and a distal end 166 of the cannulated shaft 108 both comprise slots 168A, 168B for receiving the flat connecting portion 158 of the drill tip 106. With the flat connecting portion 158 of the drill tip 106 within the slots 168A, 168B of the rigid rod 156 and cannulated shaft 108, connectors are used to rotatably secure the drill tip 106 therein.

Still referring to FIG. 7, a cannulated shaft aperture 173 extends through the distal end 166 of the cannulated shaft 108 and a rod aperture 171 extends through the distal end 164 of the rigid rod 156. A slot pin 170 extends through the rod aperture 171 and through the first aperture 160 in the drill tip 106. The slot pin 170 is firmly attached to the rigid rod 156. A pivot pin 172 extends through the cannulated shaft aperture 173 and through the second aperture 162 in the drill tip 106. The pivot pin 172 is firmly attached to the cannulated shaft aperture 173. When the cannulated shaft 108 moves proximally, the cannulated shaft 108 pulls the drill tip 106 against the rigid rod 156, causing the drill tip 106 to rotate about the pivot pin 172.

Figure 8:
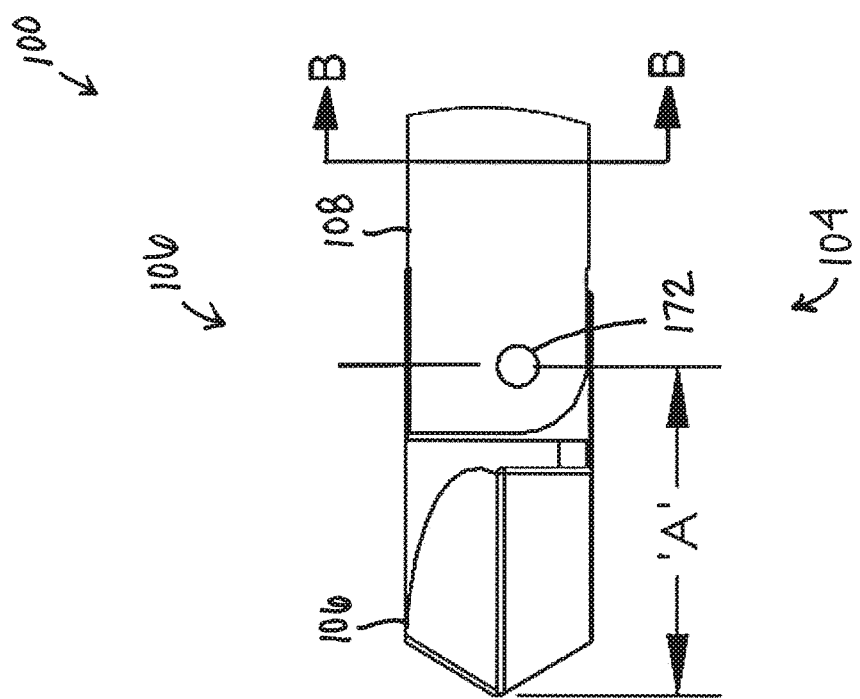
FIG. 8 is a close-up side view schematic representation of the drill tip, according to the alternative embodiment.
Figure 9:
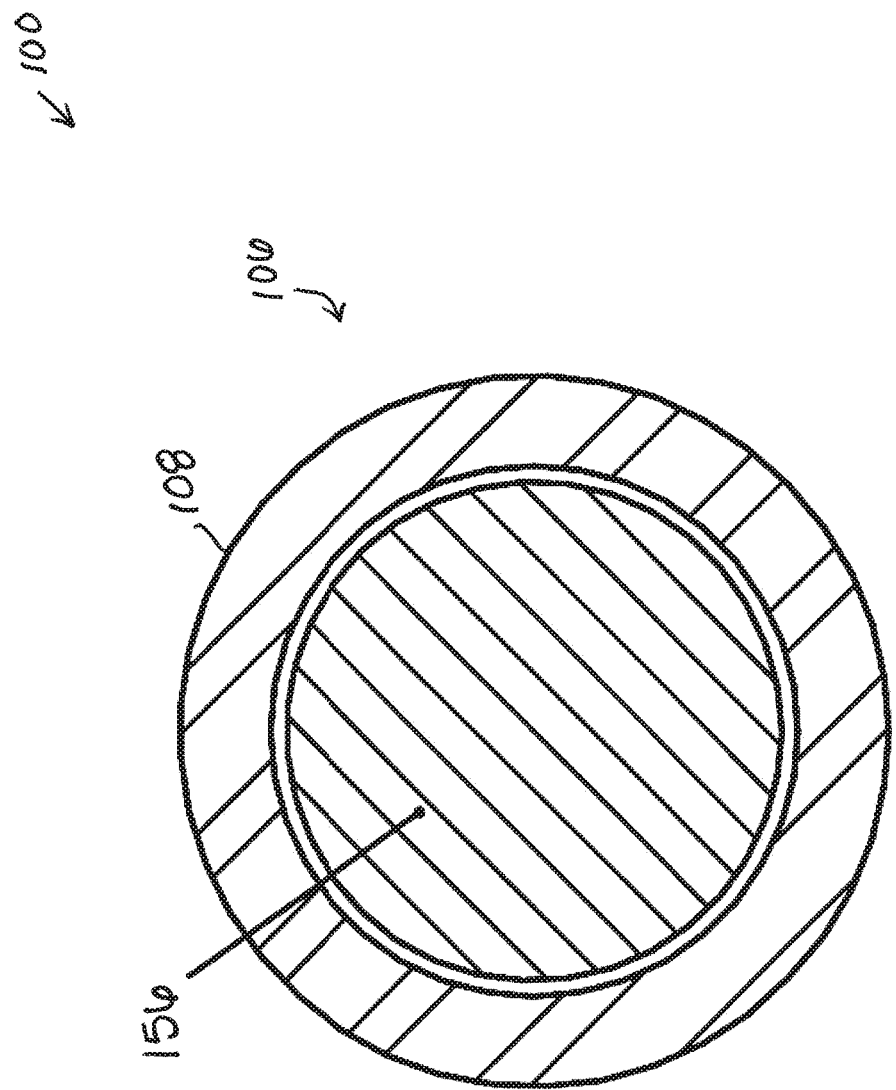
FIG. 9 is a cross-sectional view schematic representation of the drill tip in FIG. 8.

Referring now to FIG. 8, there is shown a close-up side view schematic representation of the drill tip 106, according to the alternative embodiment. The assembled distal end 104 (and drill tip 106) of the drill assembly 100 is shown. The drill tip 106 determines both the diameter of the primary (or conventional) hole and the diameter of the counterbore. The diameter of the primary hole is dictated by the diameter of the drill tip 106. The diameter of the drill tip 106 can be a variety of sizes depending on the requirements of the surgical procedure. Preferably, the diameter of the drill tip 106 is 3.5 mm. The diameter of the counterbore is determined by the distance of the pivot pin 172 and a length A of the drill tip 106. The length A is approximately half the diameter of the counterbore. FIG. 9 shows a cross-sectional view schematic representation of the drill tip 106 in FIG. 8. The cross-section shown in FIG. 9 is taken at line B-B of the drill tip 106 in FIG. 8. FIG. 9 shows the rigid rod 156 within the cannulated shaft 108. The cannulated shaft 108 is movable, while the rigid rod remains stationary.

Figure 10:
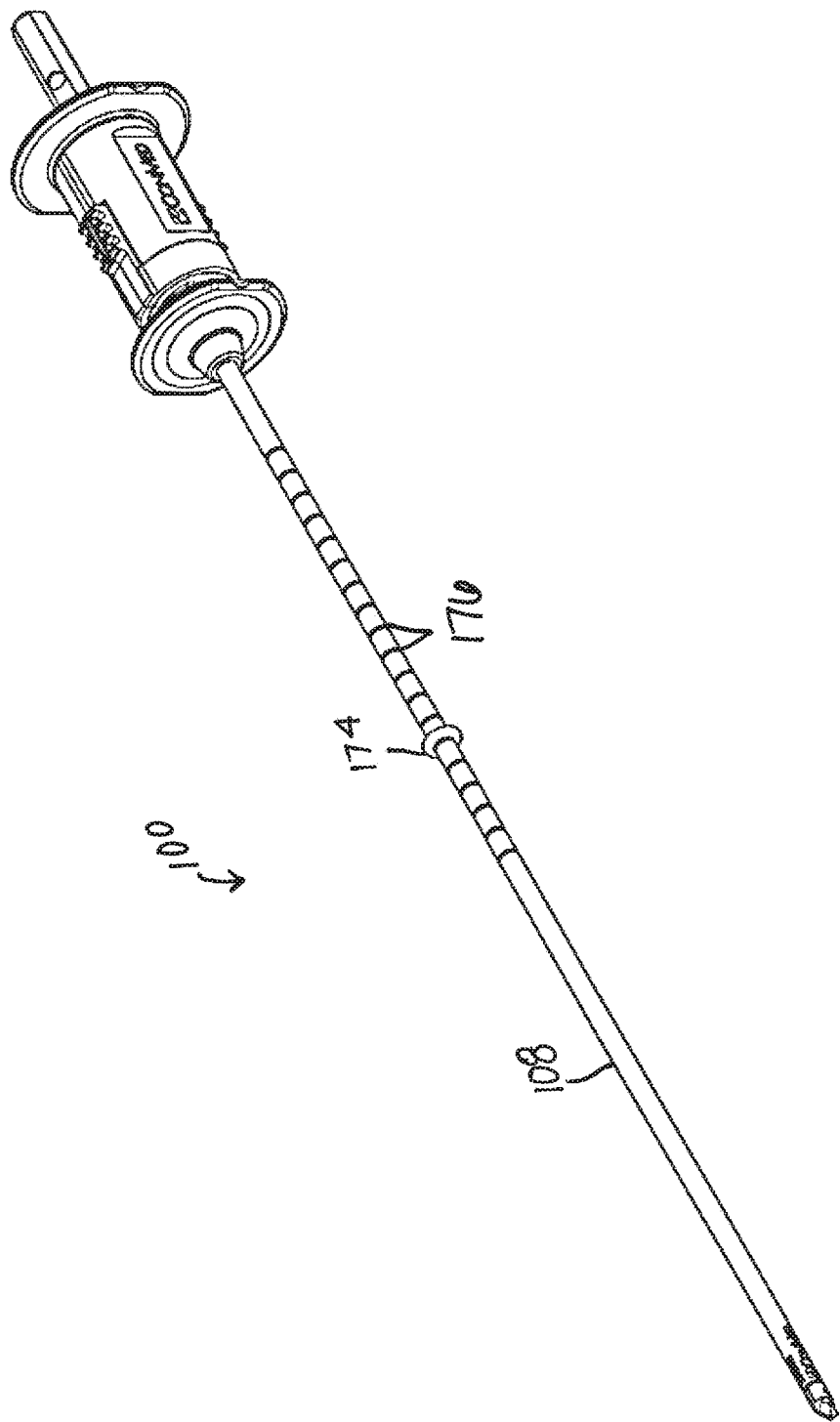
FIG. 10 is a perspective view schematic representation of a drill assembly, according to an alternative embodiment.

Turning now to FIGS. 10-21, there are shown various views schematic representations of a drill assembly 100, according to an alternative embodiment. The drill assembly 100 in FIGS. 10-21 is very similar to the drill assembly 100 in FIGS. 1-9 with a few key differences. FIG. 10 shows a perspective view schematic representation of the drill assembly 100. The drill assembly 100 comprises start indicator 174 around the cannulated shaft 108 for signaling when retrograde drilling begins. In the depicted embodiment, the start indicator 174 is a ring (e.g., an "O-ring") extending around the cannulated shaft 108. The ring 174 is configured to move anywhere along the length of the cannulated shaft 108. The ring 174 is pushed against a sleeve (not shown) and the sleeve has the cannulated shaft 108 extending therethrough. As retrograde drilling is performed, the ring 174 moves away from the sleeve and indicates the socket depth. The cannulated shaft 108 comprises a plurality of depth indicators 176 or markings along its length. In the depicted embodiment, the depth indicators 176 are laser marks and movement of the ring 174 along the laser marks 176 indicates a socket depth. In an alternative embodiment, the depth indicators 176 are grooves sized and configured to receive the start indicator 174. The grooves 176 are just deep enough to maintain the start indicator 174 therein but shallow enough that the start indicator 174 can be moved among the depth indicators 176.

Figure 11:
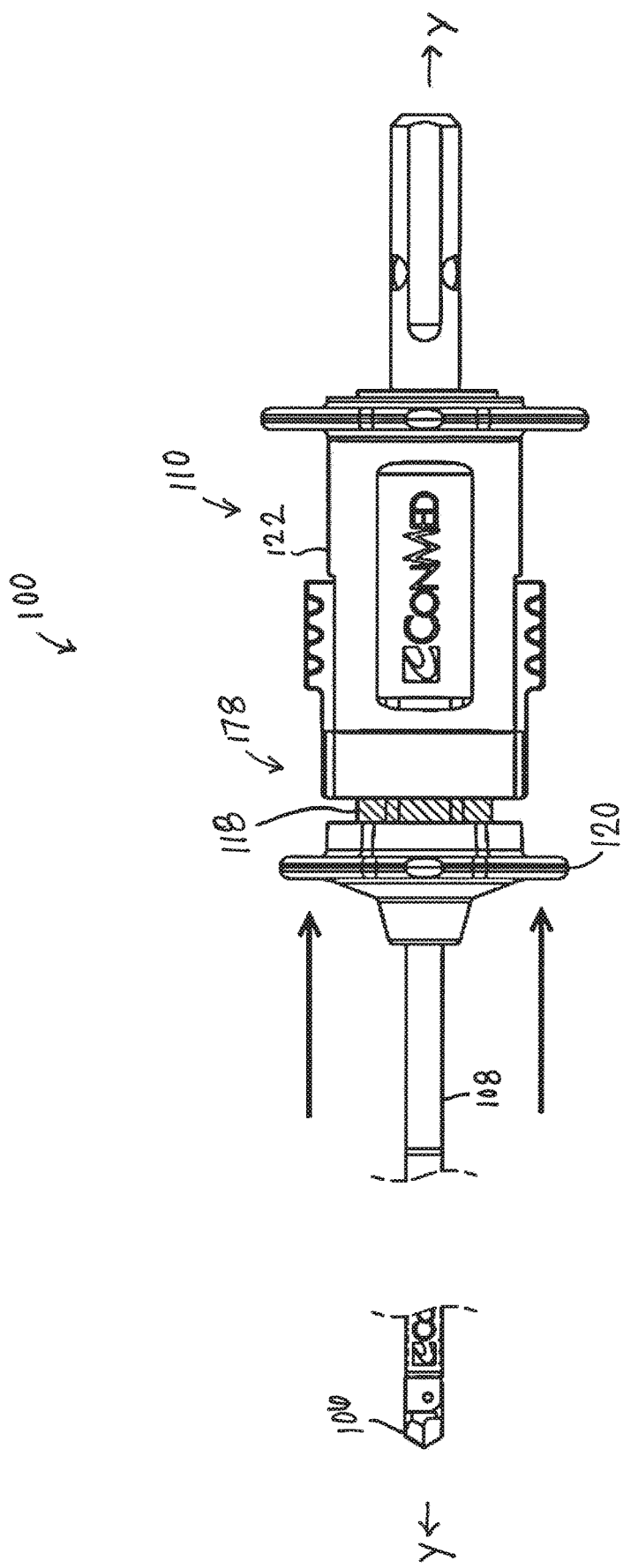
FIG. 11 is a side view schematic representation of the drill assembly in a first configuration, according to an alternative embodiment.
Figure 12:
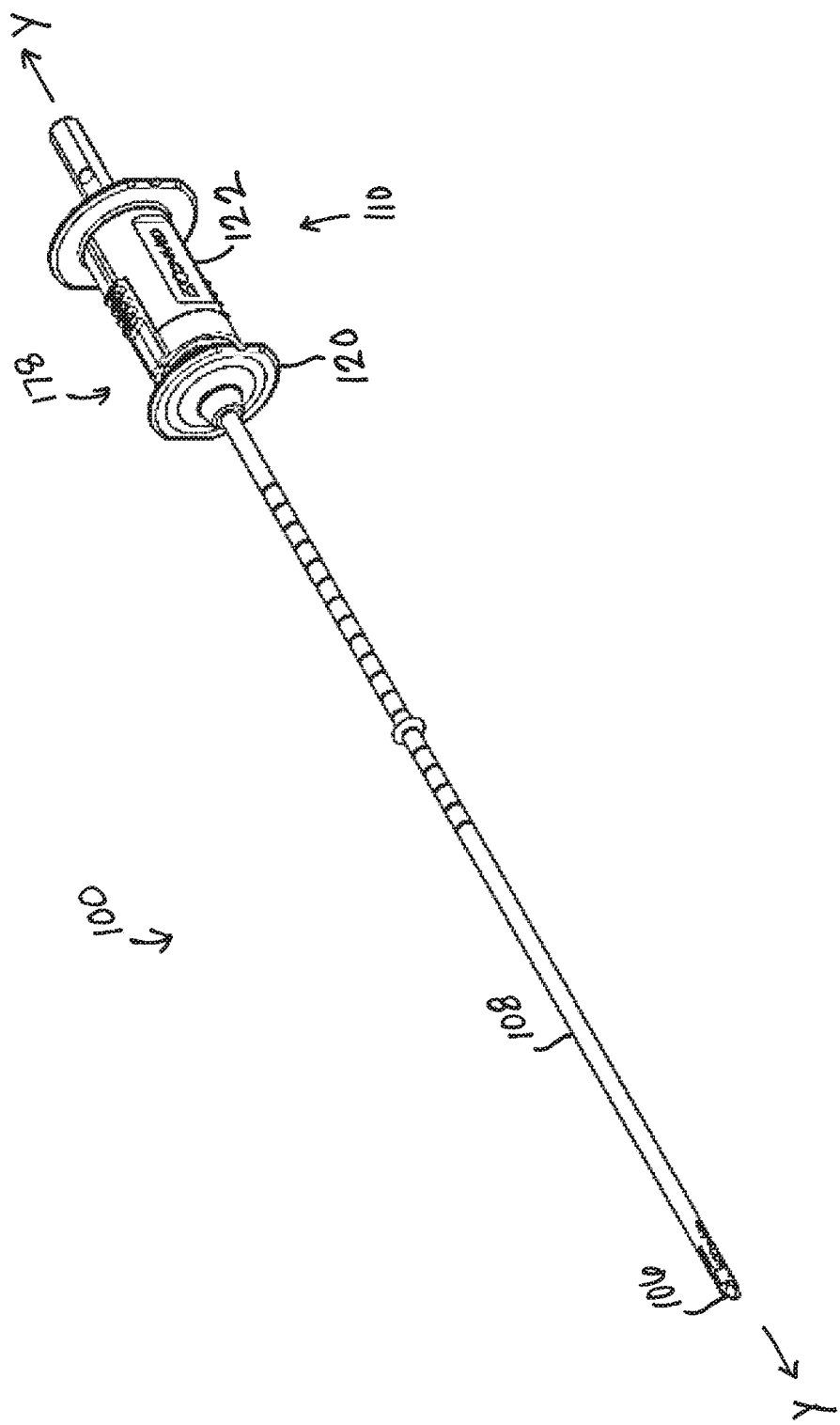
FIG. 12 is a perspective view schematic representation of the drill assembly in a first configuration, according to an alternative embodiment.

Referring now to FIGS. 11-14, there are shown perspective and side view schematic representations of the drill assembly 100 in the first and second configurations, according to an embodiment. In FIGS. 11-12, the drill assembly 100 is in the first configuration. As described above, in the first configuration, the drill tip 106 is in a 0 degree position, extending along the central longitudinal y-y axis of the drill assembly 100, as shown in FIG. 12. When the drill assembly 100 is in the first configuration, the cap 120 of the housing 110 is spaced from the distal end 178 of the body 122 of the housing 110 such that the indicator 118 between the cap 120 and the housing 110 is visible (FIG. 11).

Figure 14:
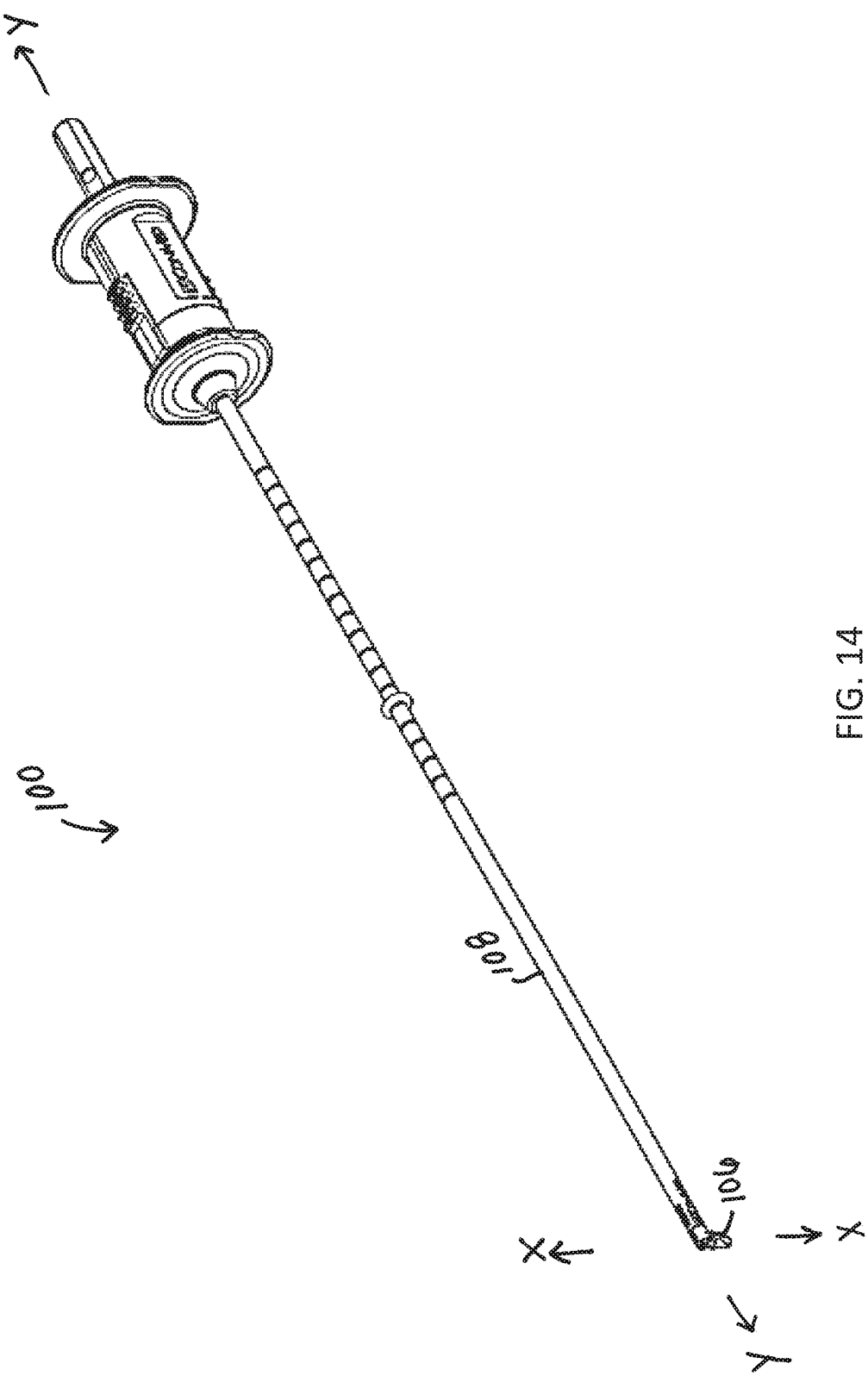
FIG. 14 is a perspective view schematic representation of the drill assembly in a second configuration, according to an alternative embodiment.

As also described above, from the first configuration, the cap 120 is pulled proximally toward the body 122 of the housing 110. When the cap 120 abuts or connects to the body 122 of the housing 110, the drill assembly 100 is in the second configuration, as shown in FIG. 13. The drill assembly 100 may also include a distal band 119 adjacent the drill tip 106. The band 119 can be laser cut into the cannulated shaft 108. The band 119 indicates the position of the drill tip 106 in the surgical site or space. Specifically, the band 119 indicates that the drill tip 106 has cleared the drilled channel and the rotating mechanism can be engaged to rotate the drill tip 106. In the second configuration, the indicator 118 is no longer visible and the drill tip 106 has rotated relative to the cannulated shaft 108 (or the drill assembly 100) and the central longitudinal y-y axis. Specifically, as shown in FIG. 14, the drill tip 106 extends along a lateral x-x axis, which is 90 degrees (or substantially perpendicular) relative to the central longitudinal y-y axis and the cannulated shaft 108 (or the drill assembly 100).

Figure 15:
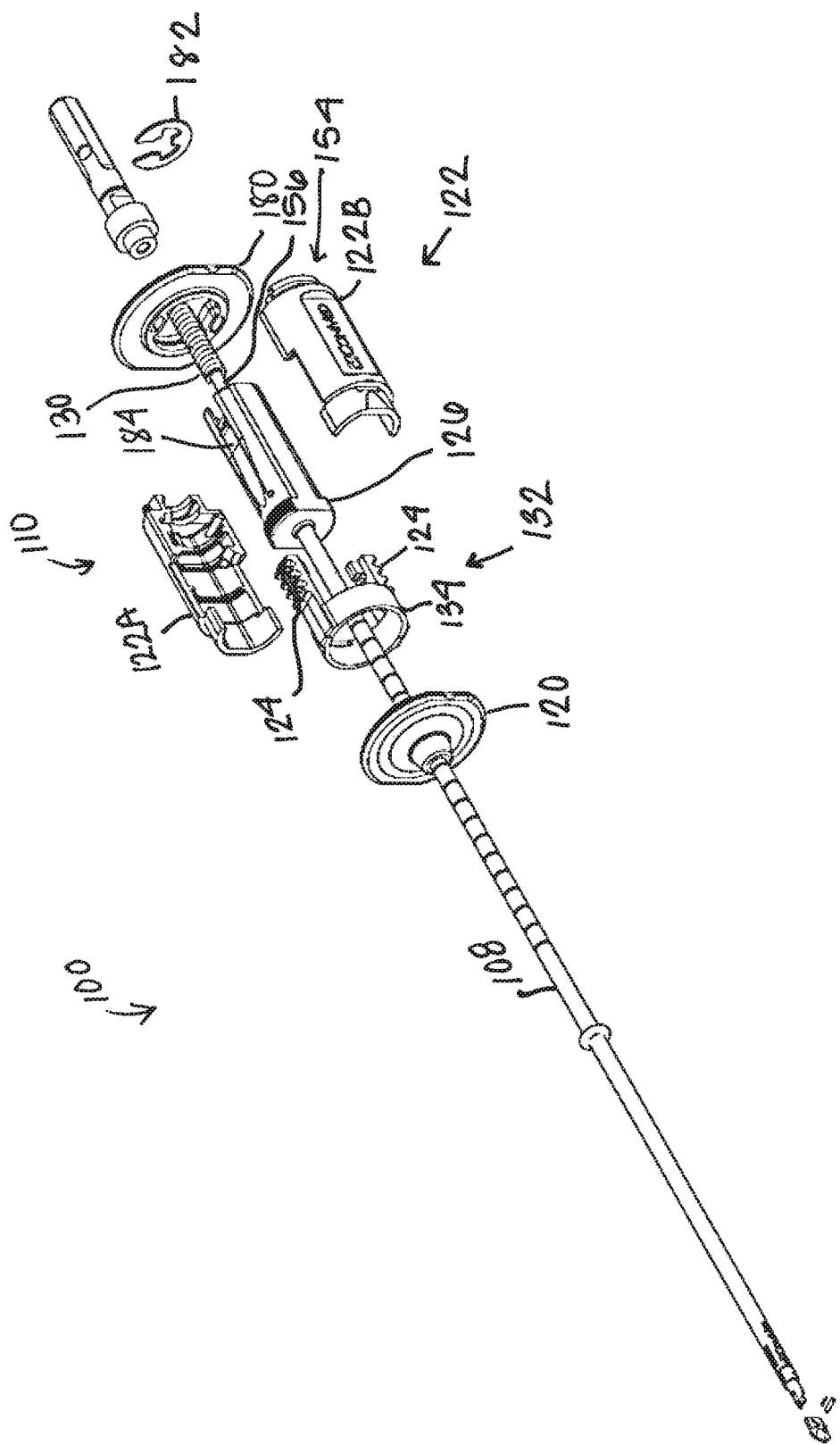
FIG. 15 is an exploded view schematic representation of the drill assembly in the first configuration, according to an alternative embodiment.

Turning now to FIG. 15, there is shown an exploded view schematic representation of the drill assembly 100, according to the alternative embodiment. In the depicted embodiment, the body 122 of the housing 110 comprises two pieces, a first portion 122A and a second portion 122B that snap or otherwise connect together. However, any number of pieces can be used for the housing 110. The internal catch and other components of the housing 110 are similar to those of the drill assembly 100 in FIGS. 1-9 with a few differences.

The housing 110 in FIG. 15 similarly includes a release 132 comprising a ring 134 with one or more release tabs 124 extending proximally therefrom. The housing 110 in FIG. 15 also similarly includes a core 126 having one or more tangs 184 extending along at least a portion of its length. The release 132 is configured to slide over the core 126 such that the release tabs 124 are positioned over the tangs 184. As shown in FIG. 15 and as described with the embodiment in FIGS. 1-9, the core 126 is securely attached to the cap 120 and the cannulated shaft 108. The housing 110 includes a proximal ring 180 (as opposed to a proximal catch 140 (FIGS. 1-9)) connected to a proximal end 154 of the body 122 of the housing 110. The proximal ring 180 holds the portions 122A, 122B of the housing 110 together. The proximal ring 180 also provides an opposing surface to a flange of the cap 120 for actuating the rotating mechanism. As shown in FIG. 15, the spring 130 extends around the rigid rod 156 between the proximal ring 180 and the core 126. The retaining ring 182 is similarly used to hold the proximal ring 180 around the rigid rod 156.

Figure 16:
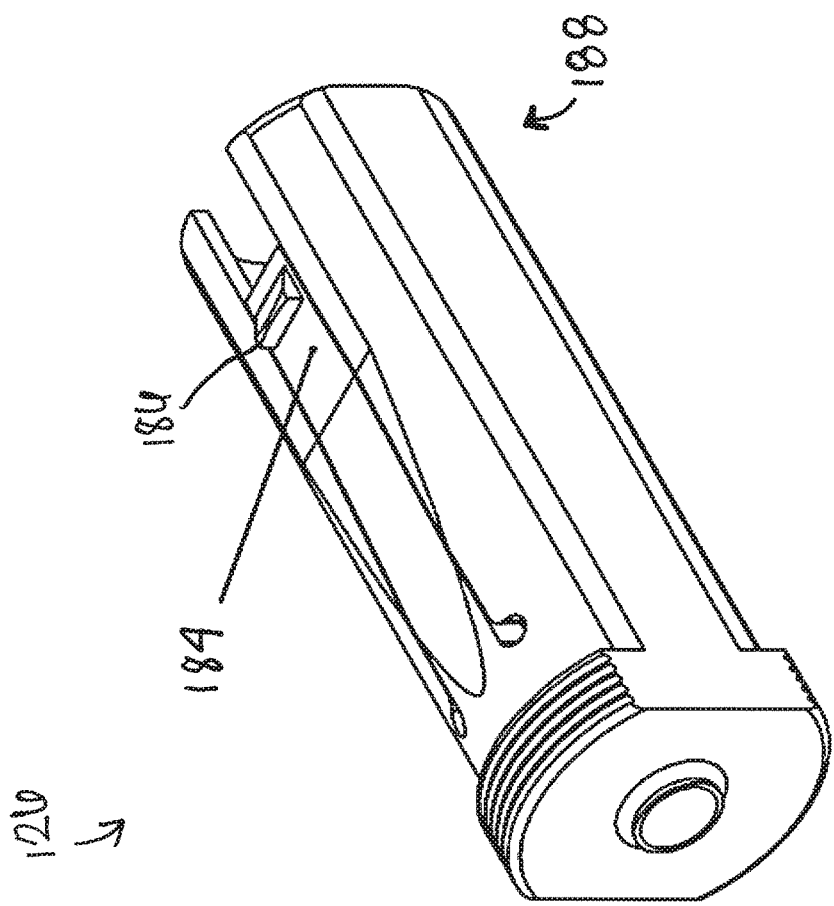
FIG. 16 is a perspective view schematic representation of the core, according to an alternative embodiment.

Referring now to FIG. 16, there is shown a perspective view schematic representation of the core 126, according to the alternative embodiment. In FIG. 16, as stated above, the core comprises one or more tangs 184 for locking the core 126 into the body 122 of the housing 110. Locking the core 126 in the body 122 maintains the drill assembly 100 in the second configuration. The tang 184 is elongated and flexible with an outward protrusion 186 near or at a proximal end 188 of the core 126.

Figure 17:
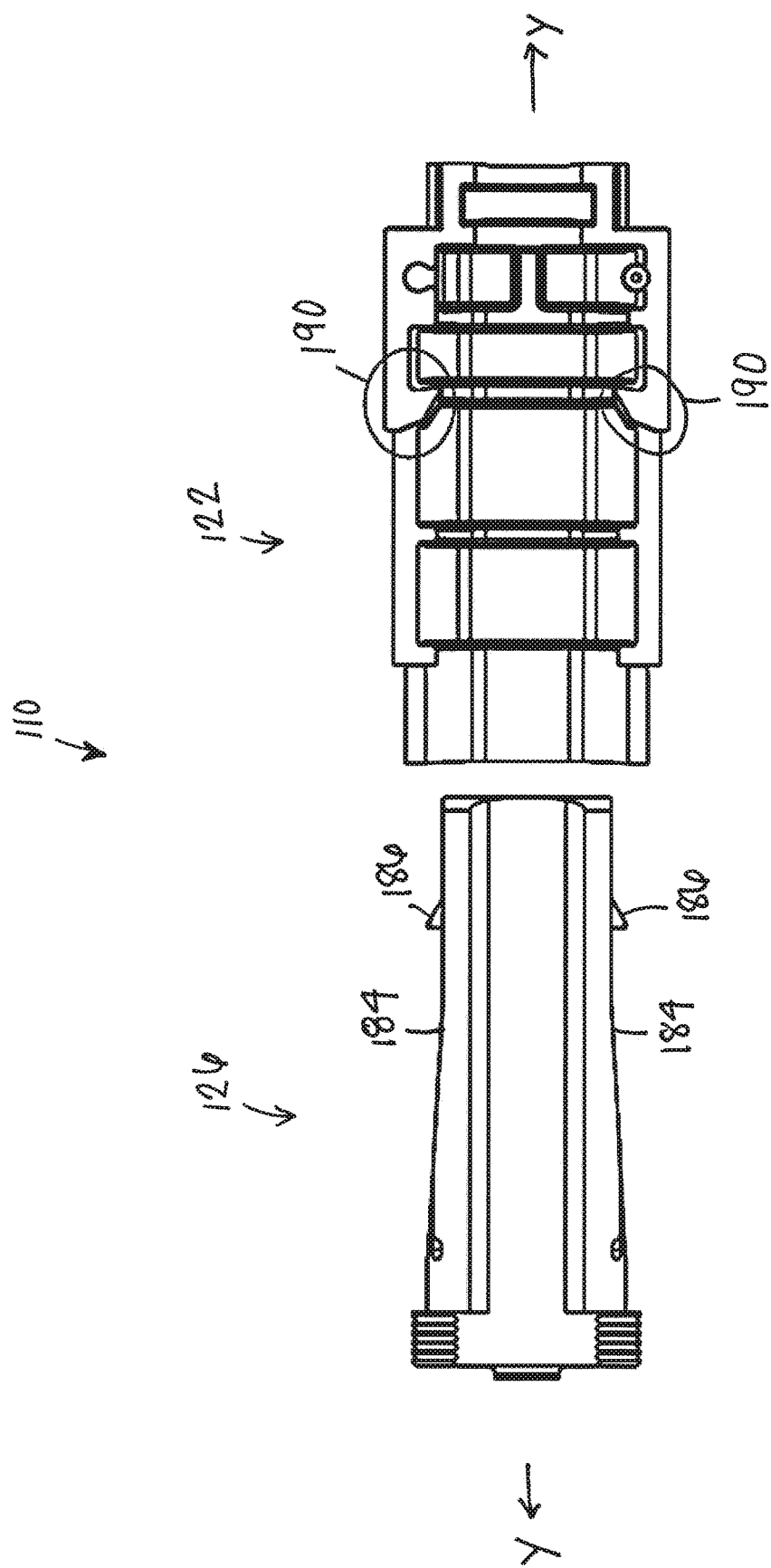
FIG. 17 is a cross-sectional side view schematic representation of the core and the body of the housing, according to an alternative embodiment.

Turning now to FIG. 17, there is a shown a cross-sectional side view schematic representation of the core 126 and the body 122 of the housing 110, according to the alternative embodiment. As shown in FIG. 17, the protrusions 186 of the tangs 184 extend outward from the central longitudinal y-y axis of the drill assembly 100. The body 122 of the housing 110 includes one or more catches 190 for engaging the tangs 184. Each catch 190 is used to keep the drill assembly 100 in the second configuration.

Figure 18:
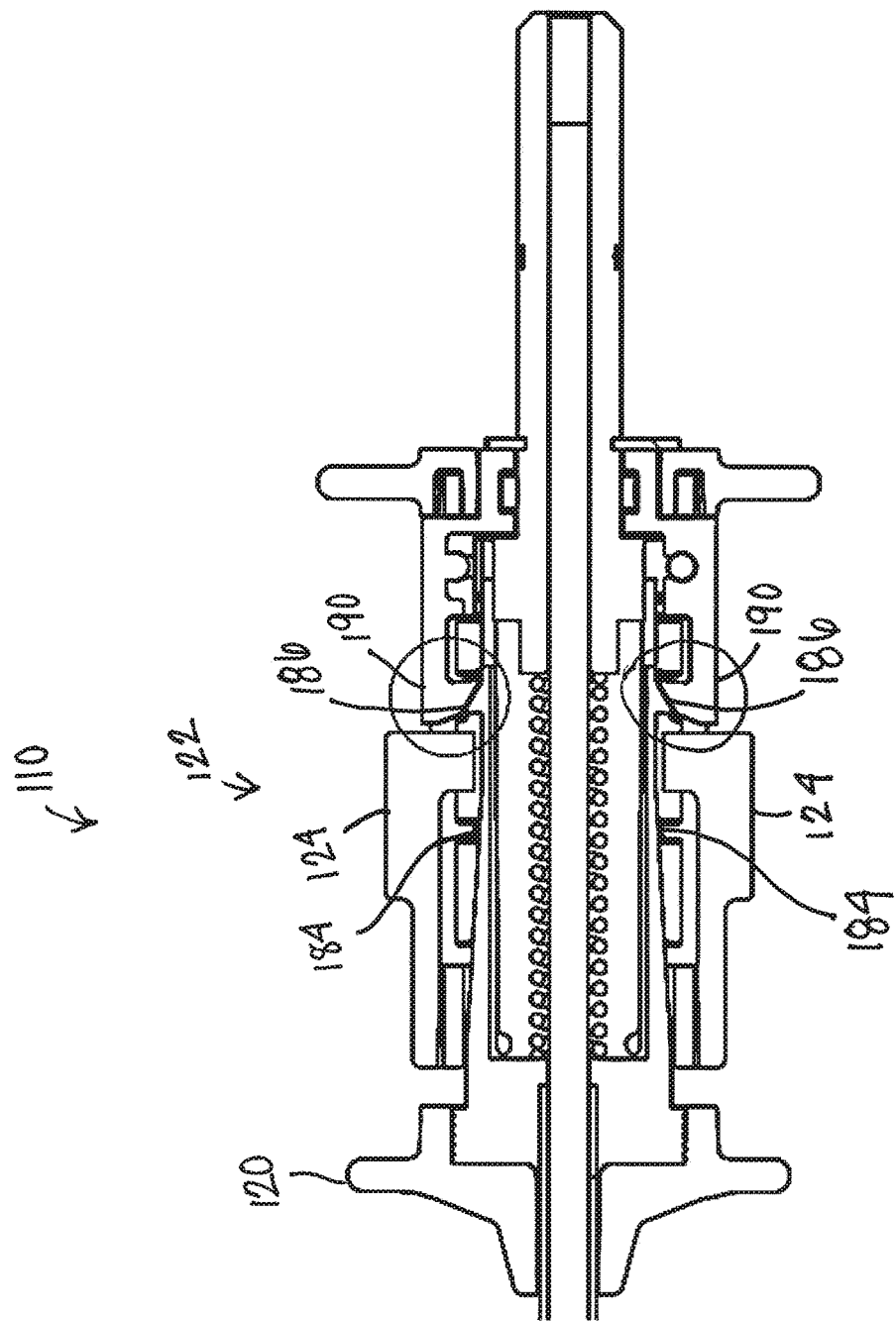
FIG. 18 is a cross-sectional side view schematic representation of the housing in the first configuration, according to an alternative embodiment.
Figure 19:
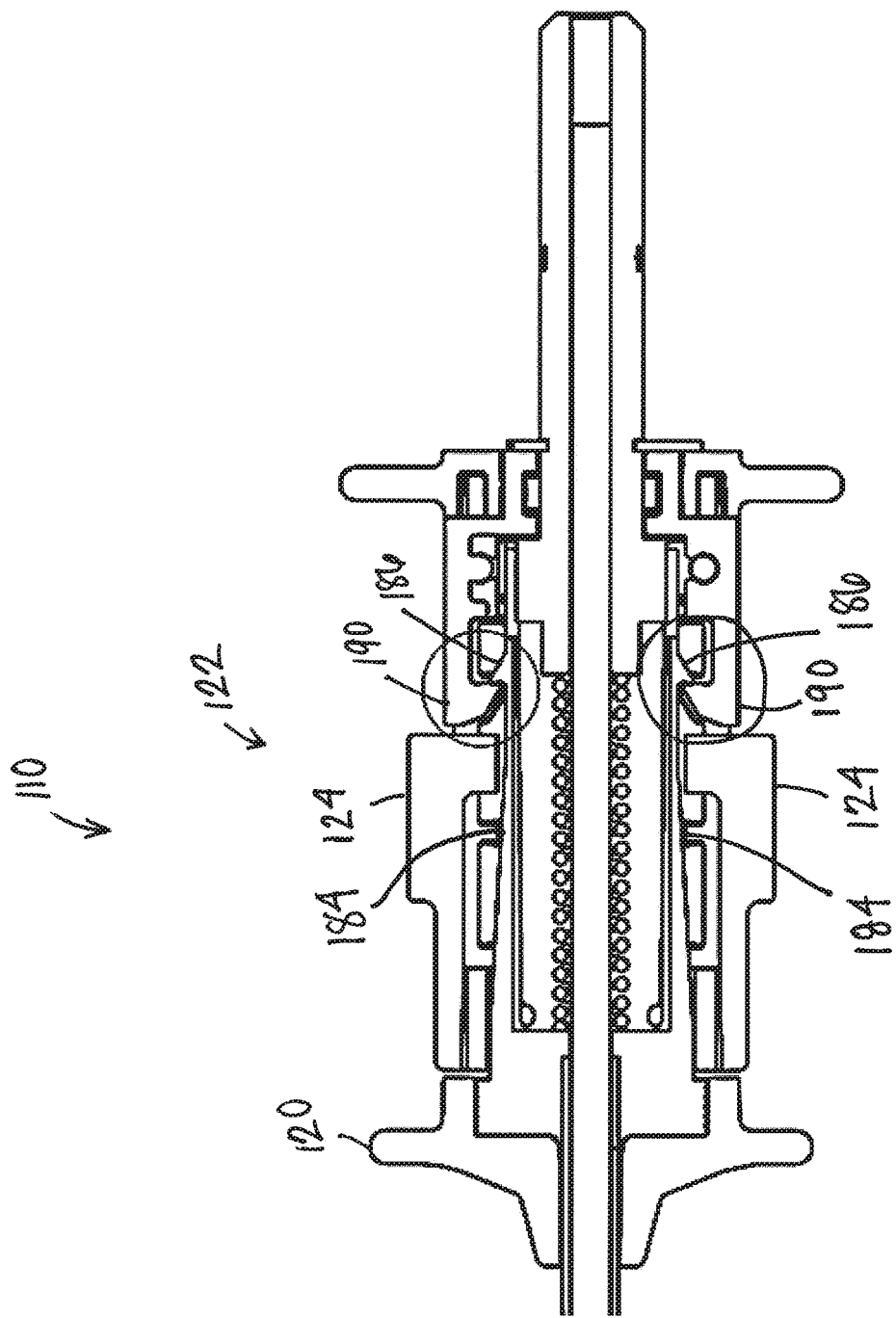
FIG. 19 is a cross-sectional side view schematic representation of the housing in the second configuration, according to an alternative embodiment.

Referring now to FIGS. 18 and 19, there are shown cross-sectional side views schematic representations of the housing 110 in the first and second configurations, respectively. In the first configuration, the catches 190 do not engage the protrusion 186 of the tangs 184, as shown in FIG. 18. In particular, the protrusions 186 are distal relative to the catches 190. When the drill assembly 100 is moved to the second configuration, the core 126 is pushed proximally into the body 122, forcing the tangs 184 and the protrusions 186 on the tangs 184 past the catches 190. The flexible nature of the tangs 184 allows the tangs 184 to flex until they past the catches 190. Once past the catches 190, the tangs 184 are no longer flexed and the protrusions 186 engage the catches 190, as shown in FIG. 19. Specifically, the catches 190 extend at least partially around the protrusions 186, holding it in place until released by pressing the release tabs 124. Pressing the release tabs 124 flexes the tangs 184 away from the catches 190 and the spring 130 (FIG. 15) forces the core 126 distally at least partially out from the body 122 of the housing 110 back to the first configuration.

Figure 20:
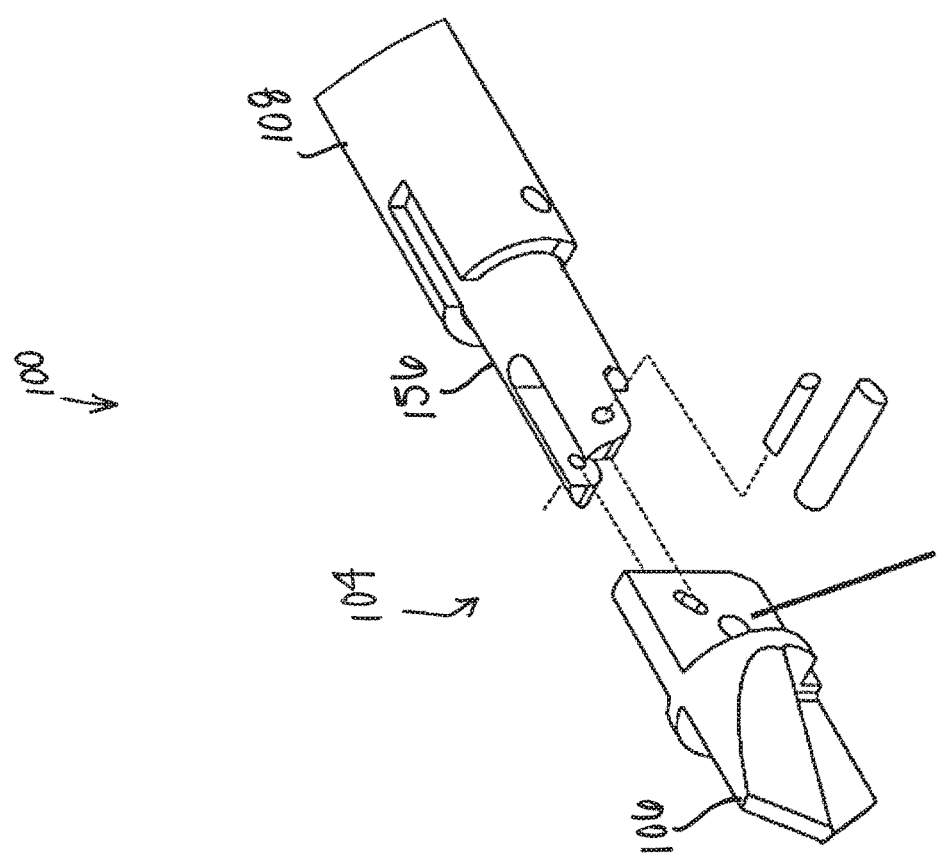
FIG. 20 is an exploded perspective view schematic representation of the distal end of the drill assembly.
Figure 21:
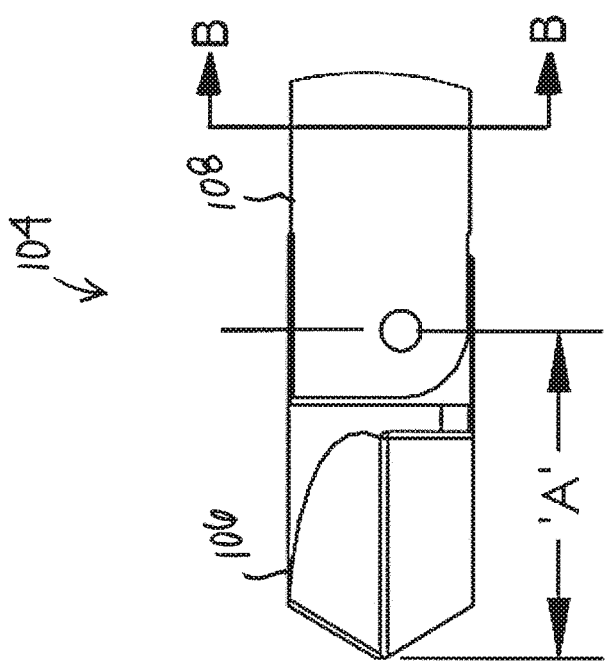
FIG. 21 is a close-up side view schematic representation of the drill tip.
Figure 22:
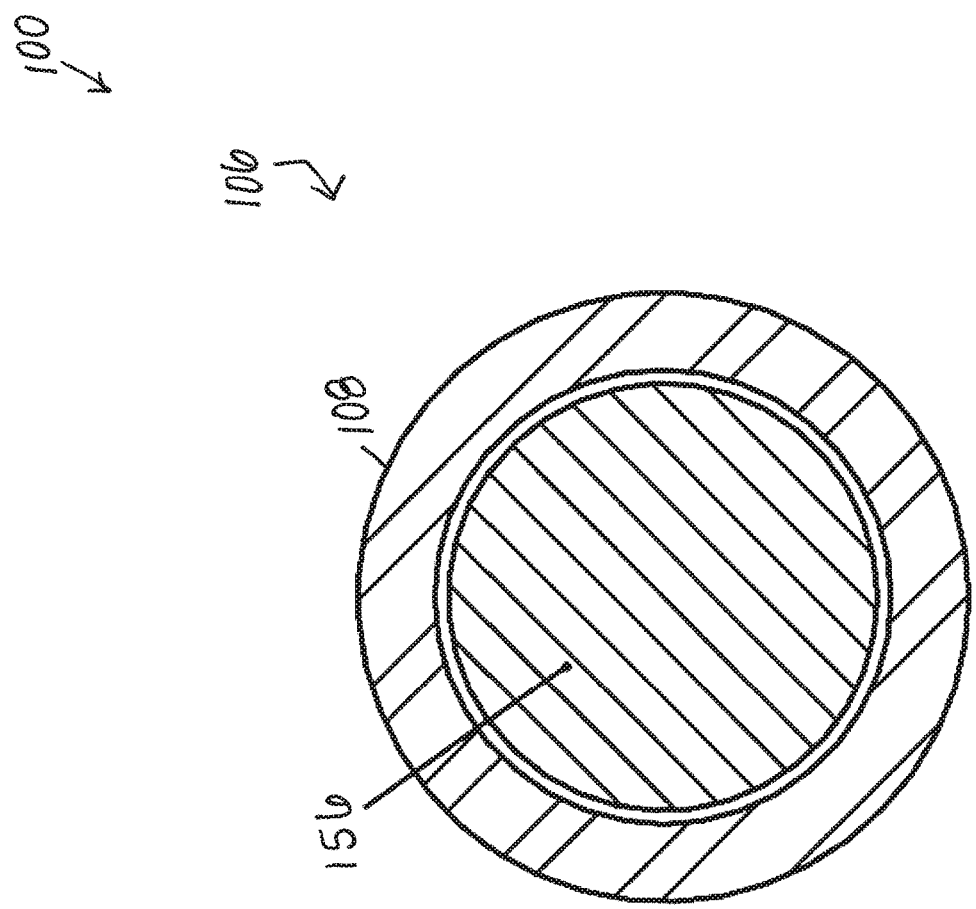
FIG. 22 is a cross-sectional view schematic representation of the drill tip in FIG. 21.

Turning now to FIGS. 20-22, there are shown various views schematic representations of the distal end 104 of the drill assembly 100, according to the alternative embodiment. FIGS. 20 and 21 show the particular attachment of the drill tip 106 to the cannulated shaft 108 and the rigid rod 156, which is the same as described above with reference to FIGS. 7 and 8. Additionally, the slidable positioning of the rigid rod 156 within the cannulated shaft 108, as shown in FIG. 22, is the same as described above with reference to FIG. 9.

All definitions, as defined and used herein, should be understood to control over dictionary definitions, definitions in documents incorporated by reference, and/or ordinary meanings of the defined terms.

While various embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings is/are used. Those skilled in the art will recognize, or be able to ascertain using no more than routine experimentation, many equivalents to the specific embodiments described herein. It is, therefore, to be understood that the foregoing embodiments are presented by way of example only and that, within the scope of the appended claims and equivalents thereto, embodiments may be practiced otherwise than as specifically described and claimed. Embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present disclosure.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprise" (and any form of comprise, such as "comprises" and "comprising"), "have" (and any form of have, such as, "has" and "having"), "include" (and any form of include, such as "includes" and "including"), and "contain" (any form of contain, such as "contains" and "containing") are open-ended linking verbs. As a result, a method or device that "comprises", "has", "includes" or "contains" one or more steps or elements. Likewise, a step of method or an element of a device that "comprises", "has", "includes" or "contains" one or more features possesses those one or more features, but is not limited to possessing only those one or more features. Furthermore, a device or structure that is configured in a certain way is configured in at least that way, but may also be configured in ways that are not listed.

The corresponding structures, materials, acts and equivalents of all means or step plus function elements in the claims below, if any, are intended to include any structure, material or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of one or more aspects of the invention and the practical application, and to enable others of ordinary skill in the art to understand one or more aspects of the present invention for various embodiments with various modifications as are suited to the particular use contemplated.

What is claimed is:

1. A drill assembly, comprising:
   a housing having an actuation mechanism, wherein the actuation mechanism
   includes a cap movable between a first position and a second position;
   a cannulated shaft connected to the actuation mechanism of the housing;
   a rigid rod extending through the cannulated shaft;
   wherein engaging the actuation mechanism moves the cannulated shaft along the rigid rod;
   a distal tip connected to the cannulated shaft and the rigid rod and comprising a most distal pointed end comprising at least two sides, wherein the distal tip extends proximally at an angle relative to a central longitudinal axis from each of the at least two sides of the most distal pointed end; and
   wherein proximal movement of the cannulated shaft along the rigid rod causes the distal tip to rotate, and
   wherein movement of the cap from the first position to the second position moves the cannulated shaft along the rigid rod and exposes or conceals a visual indicator.

2. The drill assembly of claim 1, wherein the central longitudinal axis extends through the housing.

3. The drill assembly of claim 2, wherein in a first configuration, the distal tip extends along the central longitudinal axis.

4. The drill assembly of claim 1, wherein the angle is 90 degrees.

5. The drill assembly of claim 1, further comprising a locking mechanism within the housing configured to restrict distal movement of the cannulated shaft.

6. The drill assembly of claim 5, further comprising a release mechanism on the housing configured to cause distal movement of the cannulated shaft.

7. A drill assembly, comprising:
   a housing having a cap and a body;
   a cannulated shaft connected to the cap of the housing;
   a rigid rod extending through the cannulated shaft and the cap and connected to the body of the housing such that the cannulated shaft is slidable along the rigid rod;
   wherein proximal movement of the cap causes proximal movement of the cannulated shaft along the rigid rod;
   a distal tip connected to the cannulated shaft and the rigid rod and comprising a most distal pointed end comprising at least two sides, wherein the distal tip extends proximally at an angle relative to the central longitudinal axis from each of the at least two sides of the most distal pointed end; and
   wherein the proximal movement of the cap and the cannulated shaft along the rigid rod causes the distal tip to rotate from a first configuration to a second configuration and exposes or conceals a visual indicator.

8. The drill assembly of claim 7, further comprising a core within the body of the housing, the core connected to the cannulated shaft.

9. The drill assembly of claim 8, further comprising a spring between the core and a proximal end of the housing.

10. The drill assembly of claim 8, further comprising a locking mechanism configured to lock the core within the body of the housing.

11. The drill assembly of claim 10, further comprising one or more release tabs on the housing configured to engage the locking mechanism and release the core.

12. The drill assembly of claim 7, wherein the visual indicator connects the cap to the body of the housing.

13. The drill assembly of claim 12, wherein in the first configuration, the visual indicator extends out from the body of the housing between the cap and the body of the housing.

14. A drill assembly, comprising:
- a housing having a cap and a body;
- an elongated core movable within the body of the housing, the elongated core having a cannulated shaft connected thereto and extending therefrom;
- wherein the cannulated shaft connects to and extends through the cap;
- a rigid rod extending through the cannulated shaft and the cap and connected to a proximal end of the body
- wherein the cannulated shaft and the cap are slidable along the rigid rod;
- a distal tip connected to the cannulated shaft and the rigid rod and comprising a most distal pointed end comprising at least two sides, wherein the distal tip extends proximally at an angle relative to the central longitudinal axis from each of the at least two sides of the most distal pointed end;
- wherein the proximal movement of the cap and the cannulated shaft along the rigid rod causes the distal tip to rotate from a first configuration to a second configuration and exposes or conceals a visual indicator; and
- wherein in the second configuration, the distal tip extends at an angle relative to the cannulated shaft.

15. The drill assembly of claim 14, further comprising one or more tangs extending along the elongated core.

16. The drill assembly of claim 15, further comprising one or more catches extending from the body of the housing.

17. The drill assembly of claim 16, wherein each of the one or more catches is configured to engage one of the one or more tangs.

18. The drill assembly of claim 16, further comprising a spring extending around the rigid rod between the elongated core and the proximal end of the body.

19. The drill assembly of claim 18, wherein the one or more tangs are biased distally away from the one or more catches by the spring.

* * * * *